United States Patent
Lu et al.

(10) Patent No.: US 7,486,772 B2
(45) Date of Patent: Feb. 3, 2009

(54) SYSTEMS AND METHODS FOR X-RAY IMAGING AND SCANNING OF OBJECTS

(75) Inventors: Jianping Lu, Chapel Hill, NC (US); Otto Z. Zhou, Chapel Hill, NC (US); Qi Qiu, Cary, NC (US)

(73) Assignee: Xintek, Inc., Research Triangle Park, NC (US)

( * ) Notice: Subject to any disclaimer, the term of this patent is extended or adjusted under 35 U.S.C. 154(b) by 0 days.

(21) Appl. No.: 11/601,577

(22) Filed: Nov. 17, 2006

(65) Prior Publication Data
US 2007/0206726 A1   Sep. 6, 2007

Related U.S. Application Data

(60) Provisional application No. 60/737,471, filed on Nov. 17, 2005, provisional application No. 60/787,810, filed on Mar. 31, 2006.

(51) Int. Cl.
*G01N 23/201* (2006.01)
(52) U.S. Cl. .................. 378/87; 378/6; 378/122
(58) Field of Classification Search ............ 378/4–20, 378/70, 86, 87, 122, 124
See application file for complete search history.

(56) References Cited

U.S. PATENT DOCUMENTS

| | | | |
|---|---|---|---|
| 4,891,829 A * | 1/1990 | Deckman et al. ............... 378/4 |
| 5,692,028 A | 11/1997 | Geus et al. | |
| 5,764,683 A | 6/1998 | Swift et al. | |
| 6,192,104 B1 | 2/2001 | Adams et al. | |
| 6,385,292 B1 | 5/2002 | Dunham et al. | |
| 6,553,096 B1 | 4/2003 | Zhou et al. | |
| 6,630,772 B1 | 10/2003 | Bower et al. | |
| 7,085,351 B2 | 8/2006 | Lu et al. | |
| 7,099,434 B2 * | 8/2006 | Adams et al. ............ 378/57 |
| 7,284,026 B2 * | 10/2007 | Nakayama ............ 708/400 |
| 2002/0085674 A1 | 7/2002 | Price et al. | |
| 2002/0094064 A1 | 7/2002 | Zhou et al. | |
| 2002/0140336 A1 | 10/2002 | Stoner et al. | |
| 2004/0028183 A1 | 2/2004 | Lu et al. | |
| 2004/0256975 A1 | 12/2004 | Gao et al. | |
| 2005/0129178 A1 * | 6/2005 | Pettit ............ 378/122 |

* cited by examiner

*Primary Examiner*—Jurie Yun
(74) *Attorney, Agent, or Firm*—Jenkins, Wilson, Taylor & Hunt, P.A.

(57) ABSTRACT

Systems and methods for x-ray imaging and scanning of objects are disclosed. According to one aspect, the subject matter described herein can include providing an x-ray source configured to generate a plurality of individually-controllable x-ray beams, positioning an object to be imaged in a path for intercepting at least one of the x-ray beams, activating the x-ray source, detecting intensities of the emitted x-ray beams, and generating imaging data based on the intensities for constructing an image of the object.

48 Claims, 7 Drawing Sheets

SYSTEMS AND METHODS FOR X-RAY IMAGING AND SCANNING OF OBJECTS

RELATED APPLICATIONS

This non-provisional patent application claims the benefit of U.S. Provisional Application No. 60/737,471, filed on Nov. 17, 2005, and U.S. Provisional Application No. 60/787,810, filed on Mar. 31, 2006, the disclosures of which are incorporated by reference herein in their entireties.

TECHNICAL FIELD

The subject matter described herein relates to object imaging and scanning. More particularly, the subject matter described herein relates to systems and methods for x-ray imaging and scanning of objects.

BACKGROUND

X-ray radiation technology has been used in various fields for imaging and scanning objects. For x-ray radiation technology has been used in fields such as industry manufacturing, security, biomedical/medical, electronics, security, petro-chemical, food processing and biomedical. Typical areas of application include: quality assurance, non-destructive testing (NDT) inspection, product tampering, security inspection, pipe inspection, product malfunctions and fault analysis. Transmission techniques have been applied for imaging objects. Transmission x-ray techniques typically include a high x-ray energy output of 70 keV to 200 keV. In this technique, x-rays are applied to an object, and the x-rays having sufficient energy can penetrate through the object with certain attenuation based on the object's mass attenuation coefficient. The attenuation is dominated by the photoelectric effect, which decreases very rapidly with increasing photo energy and increases greatly with the increase of the atomic number of the scanned material.

Conventional transmission-based, two-dimensional x-ray security screening systems produce a flat two-dimensional projection of the inspected object, commonly referred to as a shadowgraph. Shadowgraphs do not provide information about the three-dimensional nature of the imaged object, which can be useful for many applications. For the purpose of security screening, it is important to be able to discern the position of objects within a container. For example, in the security screening of baggage and freight, the shape of an object and the relation of the object to other objects inside a container can be important. It would be advantageous to effectively and efficiently utilize x-ray imaging techniques for obtaining three-dimensional images of objects.

Computed tomography (CT) imaging, also known as CAT (computerized axial tomography) scanning, provides an imaging technique known as cross-sectional imaging. In CT imaging, a series of projection images of an object are obtained from different viewing angles. A three-dimensional image of the object can be reconstructed to reveal the internal structure to a certain resolution based on the projection images. CT technology is widely used for medical diagnostic testing, industrial non-destructive testing, inspection of semiconductor printed circuit boards (PCBs), explosive detection, and airport security scans.

Further, backscatter x-ray techniques based on the Compton scattering effect have been applied for imaging objects. Compton scattering cross section changes with the x-ray energy and is dependent on the atomic number of the material. The differences in scattering and absorption characteristics among different material with high and low atomic numbers or their alloys provide the means to detect these two classes of materials, nominally the organic materials with low atomic number and metal material with high atomic numbers. By collecting the x-rays scattered backwards by an object, an image of the object can be obtained.

Current backscatter systems are recordings of backscattered x-ray intensities from an object penetrated by pencil beam x-ray radiation. The incident pencil beam x-ray radiation is scanned sequentially across in the time domain. Each recording can be regarded as generating one pixel of a 2-D image of the scanned object. Therefore, in order to form an image of an object, the detector has to make hundreds to millions of snap shots at different locations of the object. This process can be time consuming. Further, this process can be difficult in acquiring images of fast moving object, and thus limiting the throughput of the backscatter inspection systems.

Many x-ray sources are filament-based x-ray tubes. For example, typical x-ray tubes comprise a cathode, an anode target, and a vacuum housing. The cathode is a negative electrode that delivers electrons towards the anode target. The anode is a positive electrode that attracts and accelerates the electrons through the electric field applied between the anode and cathode. The anode is typically made of metals such as tungsten, molybdenum, palladium, silver, and copper. When the electrons bombard the target, most of their energy is converted to thermal energy. A small portion of the energy is transformed into x-ray photons radiated from the target, forming the x-ray beam. The cathode and the anode are sealed in an evacuated chamber, which includes an x-ray transparent window typically composed of low atomic number elements such as beryllium. The time to warm up the filament to generate electrons, and therefore x-ray flux is considerable long because the filament needs to be heated up to over at least 1000° C. The warm-up time required for the x-ray tube leads to imaging constraints in applications to x-ray inspections. In particular, there is a limited ability to obtain sharp images of moving objects and to switch between different x-ray beams when using systems having long warm-up times.

It is desirable to have x-ray sources for use in inspection systems that can be used to generate images showing an accurate location and shape of an object to be scanned. Further, it is desirable to have an inspection system operable to quickly switch between different x-ray imaging sources to meet an increasing demand for precisely imaging objects with different features. It is also desirable to provide the ability to controllably adjust the gain, offset, and exposure time in inspection systems to improve image optimization under a variety of conditions. Further, it is desirable to provide the ability in inspection systems to switch between different x-ray sources x-ray beam locations.

Accordingly, in view of the above described difficulties and needs, there exists a need for improved methods, systems, and computer program products for improved systems and methods for x-ray imaging and scanning of objects.

SUMMARY

The subject matter described herein comprises systems and methods for x-ray imaging and scanning of objects. One aspect can include an x-ray scanning system including a field-emission x-ray source. The x-ray source can include a field-emission cathode comprising a plurality of individually-controllable pixels configured to emit electron beams. Further, the x-ray source can include an anode positioned in an opposing relationship with the cathode and including a plurality of focal spots positioned to receive electron beams emitted by the pixels and transmit x-ray beams toward an object to be scanned from a plurality of different locations. An x-ray detector can be operable to detect the x-ray beams. A control system can be configured to control the x-ray source, the x-ray detector, and a mechanical system for positioning an object to be scanned.

Another aspect can include backscatter imaging system. The system can include an x-ray source configured to generate a plurality of individually-controllable, pulsed x-ray beams and configured to transmit the x-ray beams toward an object to be imaged. A backscatter x-ray detector can be operable to detect backscattered x-ray intensities of the plurality of x-ray beams. A control system can be configured to identify the backscattered x-ray intensities of each of the x-ray beams and configured to generate imaging data based on the identified backscattered x-ray intensities for constructing a backscattered image of the object.

The subject matter described herein can be implemented using a computer program product comprising computer executable instructions embodied in a computer readable medium. Exemplary computer readable media suitable for implementing the subject matter described herein can include chip memory devices, disc memory devices, application specific integrated circuits, programmable logic devices, and downloadable electrical signals. In addition, a computer program product that implements the subject matter herein can reside on a single device or computing platform or can be distributed across multiple devices or computing platforms.

BRIEF DESCRIPTION OF THE DRAWINGS

The subject matter described herein will now be explained with reference to the accompanying drawings of which.

DETAILED DESCRIPTION

Figure 1:
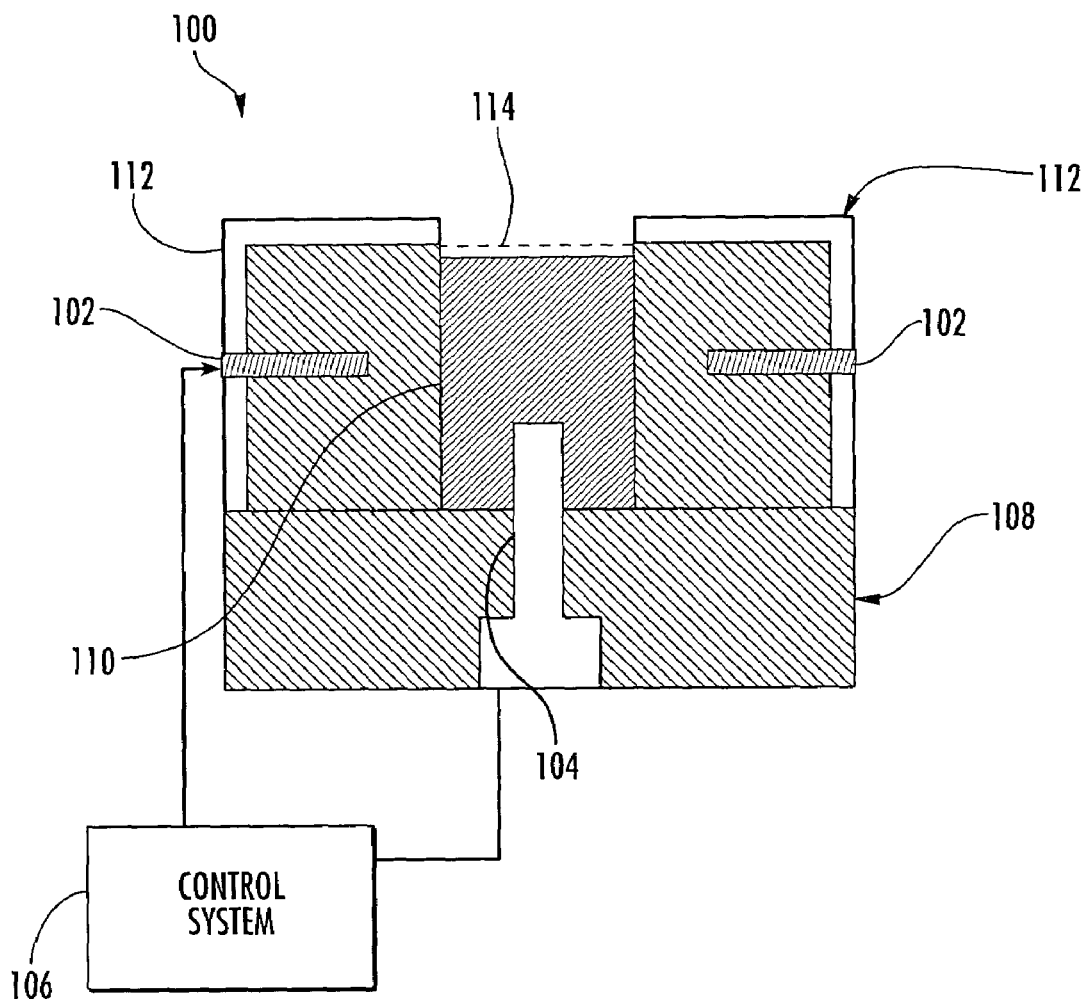
FIG. 1 is a schematic, cross-sectional side view of a field-emission triode cathode according to the subject matter described herein.

The subject matter described herein includes methods, systems, and computer program products for x-ray imaging and scanning of objects. According to one aspect, an x-ray scanning system according to the subject matter described herein can include a field-emission cathode comprising a plurality of individually-controllable pixels configured to emit electron beams. The pixels can be arranged substantially along circumferences of a plurality of concentric circles or in a two-dimensional matrix. Further, the pixels can have different sized emission areas. The electron beams can be emitted towards an anode positioned in an opposing relationship with the cathode. The anode can include a plurality of focal spots positioned to receive an electron beam emitted by a respective pixel. The pixels and focal spots can be arranged in any suitable shape. For example, the pixels and focal spots can be arranged in an at least substantially circular shape or in an at least substantially linearly shape. The anode can generate a plurality of x-ray beams in response to being bombarded by the electron beams such that x-ray beams are transmitted toward an object to be scanned. The x-ray beams can be transmitted toward the object from different locations such that the object to be scanned is imaged from several different directions. The x-ray scanning system can include one or more x-ray detectors operable to detect the generated x-ray beams. Further, a control system can control the x-ray source, the x-ray detector, and a mechanical system for positioning the object to be scanned in the path of the x-ray beams. The control system can individually control each of the pixels such that x-ray beams are generated simultaneously from different locations or generated in a predetermined sequence from different locations.

In another aspect, a backscatter imaging system according to the subject matter described herein can include an x-ray source configured to generate a plurality of individually-controllable, pulsed x-ray beams. The x-ray source can be configured to transmit the x-ray beams toward an object to be imaged from different directions. A backscatter x-ray detector can be configured to detect backscattered x-ray intensities of the plurality of x-ray beams. A control system can be operably connected to the x-ray source and the x-ray detector. Further, the control system can control the x-ray source to generate the x-ray beams simultaneously or in a predetermined sequence. Further, the control system can be configured to identify the backscattered x-ray intensities of each of the x-ray beams and to generate data imaging data based on the identified backscattered x-ray intensities for constructing a backscattered image of the object.

X-ray sources in accordance with the subject matter described herein can include a field-emission cathode and can be implemented in a simple diode mode. In the diode mode, a bias voltage can be applied between a target anode and a cathode for generating an electrical field. Electrons are emitted from the cathode when the electrical field exceeds a threshold field for emission. The field-emission cathode can include a plurality of individually-controllable pixels that can comprise nanostructure-containing material. In one example, the nanostructure-containing material can include single-walled carbon nanotubes, multi-wall nanotubes, or mixtures of single-walled carbon nanotubes and multi-wall nanotubes. Carbon nanotubes have large field enhancement factors ($\beta$). Further, carbon nanotubes are stable at high currents. A stable emission current of greater than 1 μA has been observed from an individual single-walled carbon nanotube and an emission current density greater than 1 A/cm$^2$ from a macroscopic cathode containing such material has been reported. These properties make carbon nanotubes attractive electron field emitters for field emission x-ray devices. The pixels can be housed individually or housed together in an integrated housing.

In another example, cathode pixels can include a coating layer of nanostructure-containing material on a substrate material. Further, an adhesion-promoting interlayer can be disposed between the substrate material and the coating layer of nanostructure-containing material.

In one application of the subject matter described herein, the systems described herein can be used for examining concealed or embedded object features for inspecting fully assembled components in-line and in three dimensions for a wide range of materials. Further, the systems described herein can generate real-time, three-dimensional x-ray images of objects as the objects are being screened by an operator. For security screening applications, the benefits of providing three-dimensional images include, for example, reduced operator training time, reduced evaluation time per bag for providing higher throughput, reduced false alarm rates, reduced "hand-search" time through targeted examination, and overall increase in safety, security, and efficiency. It is important in screening applications to be able to ensure the quality and reliability of objects, particularly in respect of safety critical items. The systems and methods described herein can provide real-time x-ray inspection of objects.

According to one embodiment, a field-emission cathode can include one or more triode cathodes. For example, one pixel of an x-ray source can correspond to a single triode cathode. Further, the field-emission cathode can be a cold cathode. FIG. 1 is a schematic, cross-sectional side view of a field-emission triode cathode generally designated 100 according to the subject matter described herein. Referring to FIG. 1, field-emission triode cathode 100 can be activated to emit an electron beam for generating x-ray emissions. A gate electrode 102 and a cathode including nanostructure field emitters 104 can be spaced a distance 50 to 500 micrometers from the emitter surface. Electrons can be extracted by applying a bias field between gate electrode 102 and cathode 104. Also, the electron current and energy can be controlled separately by a control system 106. In particular, control system 106 can include a power supply configured to apply voltage to gate electrode 102, cathode 104, and the anode. Exemplary x-ray beams that can be emitted by system 100 include x-ray fan beams and x-ray pencil beams.

System 100 can include an insulator 108 and a metal insert 110. Insulator 108 can electrically isolate cathode 104 from other nearby electrical components. Metal insert 110 can be coated with the nanostructure field emitters of cathode 104 on at least one side. Further, system 100 can include a metal shell 112 and a mesh grid 114. Mesh grid 114 can be electrically insulated from metal insert 110 by offsetting the height between metal insert 110 and a slot within insulator 108. The offset distance can be smaller than about 200 μm.

The overall shape of a triode cathode can be cubical or cylindrical. Exemplary insulating materials of the triode cathode can include ceramic and mica. Mesh grid 114 can be made of nickel, molybdenum, tungsten or other high melting temperature materials.

Figure 2:
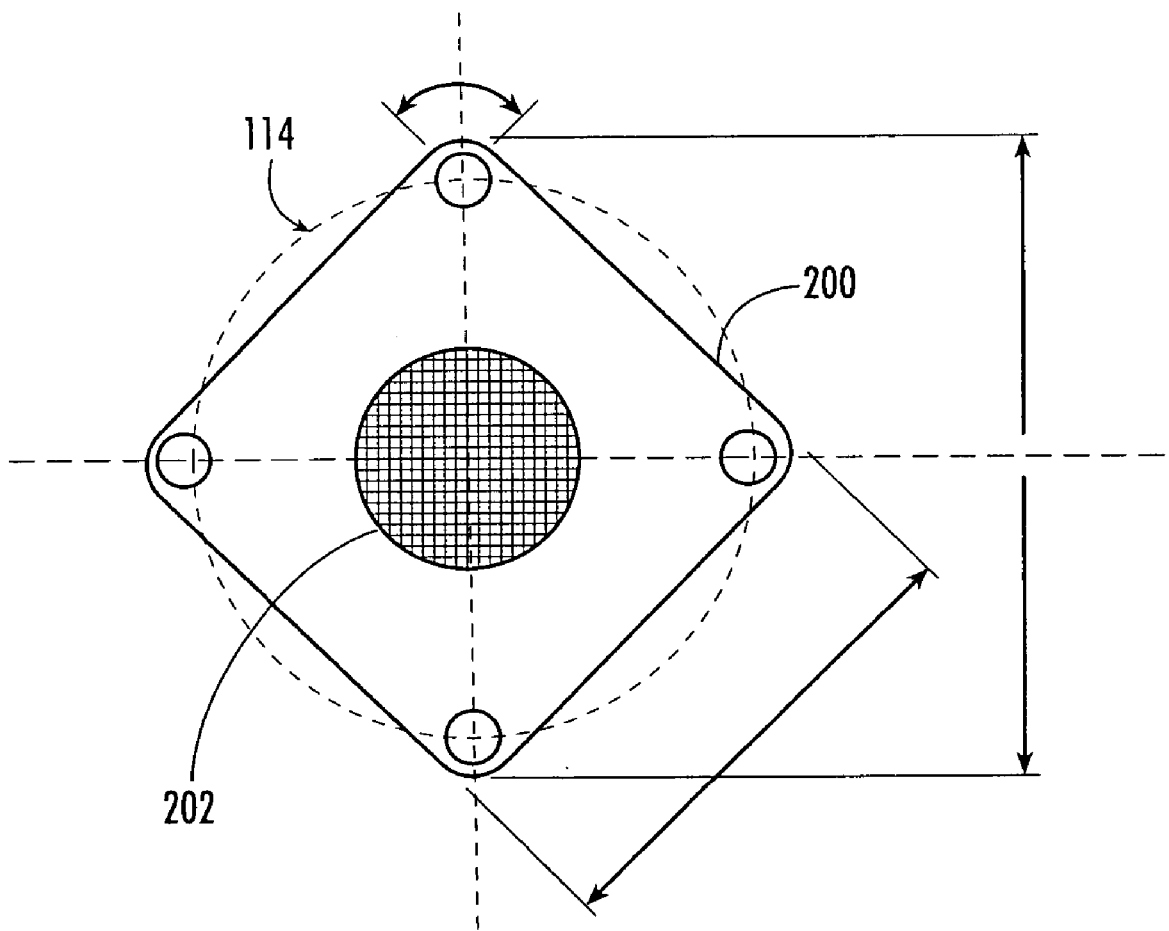
FIG. 2 is a top view of a mesh grid according to an embodiment of the subject matter described herein.

FIG. 2 is a top view of mesh grid 114 according to an embodiment of the subject matter described herein. Referring to FIG. 2, mesh grid 114 can have a frame 200 with a mesh opening 202 that can be at its center. Mesh opening 202 can have a diameter between about 10 μm and about 100 μm. The diameter of the wires can be in the range of about 10 μm to about 100 μm. A high physical transmission rate of greater than 50% can be utilized.

Figure 3:
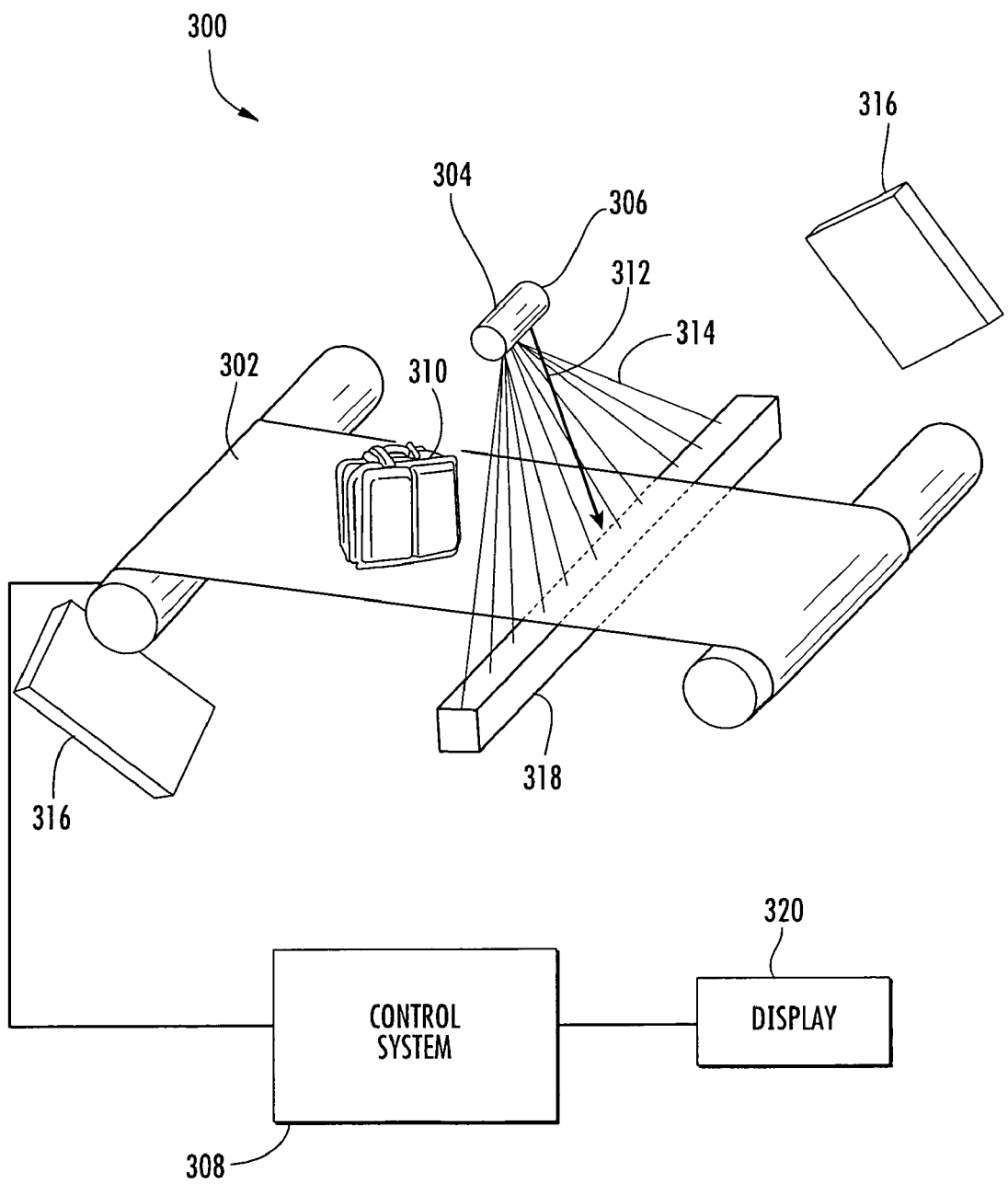
FIG. 3 is a top perspective view of an x-ray scanning system according to an embodiment of the subject matter described herein.

FIG. 3 is a top perspective view of an x-ray scanning system generally designated 300 according to an embodiment of the subject matter described herein. System 300 can include a single field-emission cold cathode based x-ray source. The source can include an anode and cathode positioned in the interior of a vacuum chamber. Referring to FIG. 3, system 300 can include a conveyor 302, an independently controllable fan beam x-ray source 304, and an independently controllable pencil beam x-ray source 306. Conveyor 302 can be controlled by a control system 308 to move an object 310 to be scanned in position for intercepting an x-ray fan beam 314 emitted by x-ray source 304 and an x-ray pencil beam 312 emitted by x-ray source 306. While conveyor 302 is unnecessary in that a stationary object can be scanned, any mechanical system can be used to position object 310. Further, system 300 can include backscatter x-ray detectors 316 and a transmission x-ray detector 318 operable to detect backscattered x-ray beams and transmission x-ray beams, respectively. Detectors 316 and 318 can comprise an array of detector pixels. Control system 308 can control the generation of x-ray beams by x-ray sources 304 and 306 and the detection of x-ray beams by x-ray detectors 316 and 318. Alternatively, more than one fan beam x-ray source and more than one pencil beam x-ray source can be utilized for applying x-ray beams to object 310.

Backscatter x-ray detectors 316 can be positioned for collecting x-rays scattered by object 310. For example, a backscatter x-ray detector placed in front of object 310, behind object 310, above object 310, or below object 310. The x-rays detected by detectors 316 can be obtained and converted into signals for use in constructing a visible image.

Transmission x-ray detector 318 can be shaped linearly for receiving transmitted x-ray beam 314 from x-ray source 304. Alternatively, a transmission x-ray detector 318 can be formed in an "L" shape and positioned placed such that it can detect the incident x-ray after it is attenuated by scanned object 310. The x-rays detected by detector 318 can be obtained and converted into signals for use in constructing a visible image.

The x-ray sources of system 300 can include a plurality of pixels made of a field-emission triode and/or a diode cathode in x-ray sources for generating x-ray beams. The generated x-rays can be converted to an x-ray fan beam by using a collimator. Further, a generated x-ray fan beam can be converted to an x-ray pencil beam by applying an additional collimator or a chopper with open slots.

Control system 308 can comprise suitable hardware, software, and/or firmware components for controlling the components of system 300. System 308 can be programmed to individually control the x-ray beams emitted by x-ray sources 304 and 306, the movement of conveyor 302, the collection of signals by detectors 316 and 318, and the process, construction and analyses of the images. System 300 can comprise a display 320 for displaying images. Alternatively, system 300 can comprise a plurality of monitors for displaying different views of scanned objects.

X-ray sources 304 and 306 can be controlled by control system 308 to operate in a pulse mode for generating x-ray beam pulses of a predetermined frequency. Control system 308 can control the pixels of x-ray sources 304 and 306 to be activated at a predetermined frequency and duty cycle. The duration of the x-ray on time and the frequency of the x-ray radiation can be programmed into control system 308. In one example, the x-ray fan beam and x-ray pencil beam generated by x-ray sources 304 and 306, respectively, can be alternatively turned on at a high frequency. In this example, only one beam is used to radiate object 310 at any one time. In this manner, the transmission x-ray signal and backscatter x-ray signal can be separated in the time domain. The signal detected by transmission x-ray detector 318 can in this arrangement be only from transmission x-ray source 306. The signal detected by backscatter x-ray detectors 316 can originate only from x-ray pencil beam 312. Therefore, both transmission x-ray images and scatter x-ray images can be available to the operator in a timely basis by switching between the two x-ray sources. By increasing the operation frequency, both kinds of images can be obtained almost simultaneously. These can be especially helpful for scanning an object having a mixture of properties.

Control system 308 can be configured to apply sine-based, cosine-based, triangle wave-based, and square wave-based modulation to the x-ray source, including those of a predetermined frequency and predetermined peak amplitude. Also, the predetermined frequencies can be orthogonal, and the control system can apply temporal Fourier transform based on orthogonal frequency division multiplexing (OFDM). Control system 308 can also perform temporal Fourier transformation of intensity versus time data detected by backscatter x-ray detector 316, determine the intensity contribution from each x-ray beam based on spectrum in a frequency space based on the temporal Fourier transformation, and construct a plurality of backscattered images from each x-ray beam based on the determined intensity contribution. Also, control system 308 can process the detected x-ray beams using an inversion Hadamard transformation matrix for constructing an image on display 320.

Figure 4:
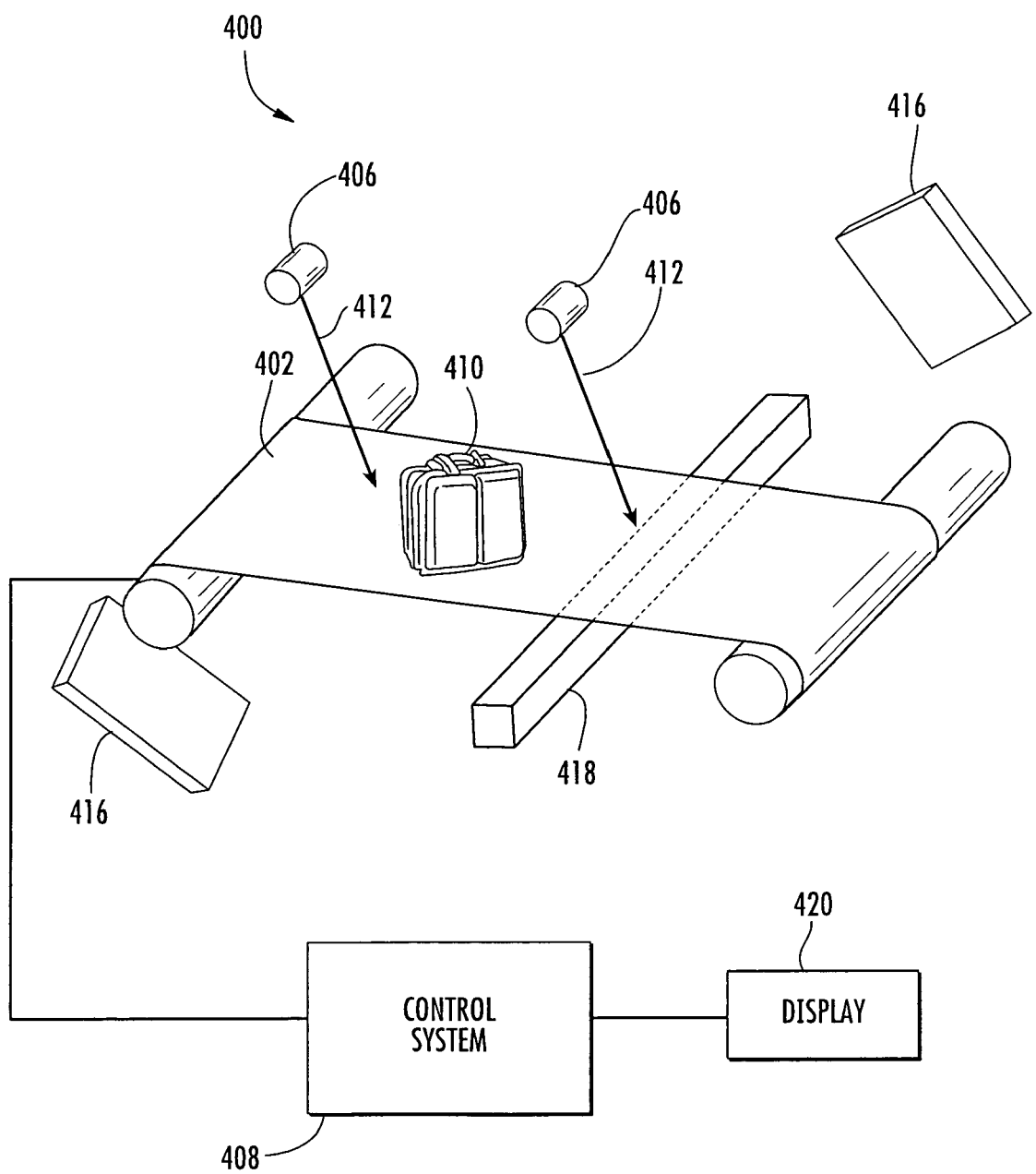
FIG. 4 is a top perspective view of an x-ray scanning system according to another embodiment of the subject matter described herein.

In one embodiment, as shown in FIG. 4, a system 400 can comprise multiple field-emission cold cathode based x-ray sources, as shown in FIG. 4. Multiple cold cathode-based x-ray sources 406 can be configured to generate x-rays beams 412 from different locations and angles with respect to an object 410 to be scanned. Multiple such x-ray sources can be employed and collimated to form fan x-ray beams and pencil x-ray beams from different locations. Transmission x-ray detectors 418 can be used to collect the x-rays transmitted through the scanned objects to form images from different angles. Also, backscatter x-ray detectors 416 can be used to collect backscatter x-ray to form two-dimensional or three-dimensional images. The different images can be utilized and analyzed to reveal the internal structure of objects with different features.

A multi-beam x-ray imaging or scanning system in accordance with the present disclosure can comprise one or more stationary field-emission cathode based x-ray sources for generating an x-ray fan beam or beams. Further, the system can comprise one or more stationary field-emission cathode-based x-ray sources for generating an x-ray pencil beam or beams. The system can also comprise one or more transmission x-ray detectors and backscatter x-ray signal detectors placed at predetermined locations. The system can comprise an x-ray filter positioned to receive at least one of the x-ray beams to generate an x-ray pencil beam or an x-ray fan beam. The system can also comprise a chopper that can be controllably movable with an aperture that can be circular or slotted in shape for passing an x-ray beam therethrough. The system can further comprise a power supply to supply power to the field-emission x-ray source, the x-ray detector, and the control system, which can all be integrated in a housing. Also, the x-ray detector and the field-emission x-ray source can be in a common hemisphere with respect to the object to be scanned.

An object 310 can be scanned by a system 300 in accordance with the subject matter described herein with fan and pencil x-ray beams directed at object 310 from different locations. A control system 308 can control the activations of pencil x-ray beam 312 and fan x-ray beam 314 such that only one of the beams is turned on at any time. Further, a signal can be collected by transmission x-ray signal detectors 318 only from the fan beam x-ray source 304 during the time that x-ray fan beam 314 is transmitting. Further, a signal can be collected by the backscattered x-ray detectors 316 only from the pencil x-ray beam source 306. Also, the two different x-ray sources can switch on and off in a high-speed fashion whereby both types of x-ray images can be acquired at least substantially simultaneously. Either one of these two different x-ray sources can be used independently to form one only type of image at a time.

In one embodiment, referring to FIG. 4, system 400 can comprise two sources for generating x-ray pencil beams. The x-ray pencil beams can be directed at object 410 from different locations. Further, the path of the beams 412 can be co-planar. Alternatively, the x-ray pencil beams can be directed perpendicular to the moving direction of the scanned object. Furthermore, the pencil x-ray beams 412 can be turned on one at one time and the backscatter x-ray detectors 416 can detect the scattered signal from only one of the sources at one time. Alternatively, the pencil x-ray beam sources 406 can be placed at different positions along the moving direction of object 412 and each pencil beam 412 can be individually controllable so that pencil beams 412 can be turned on selectively in a programmable pattern. By gathering and analyzing the signals from backscatter x-ray detectors 416 from different x-ray pencil beams, an accurate image of the scanned object can be formed on display 420.

Figure 5:
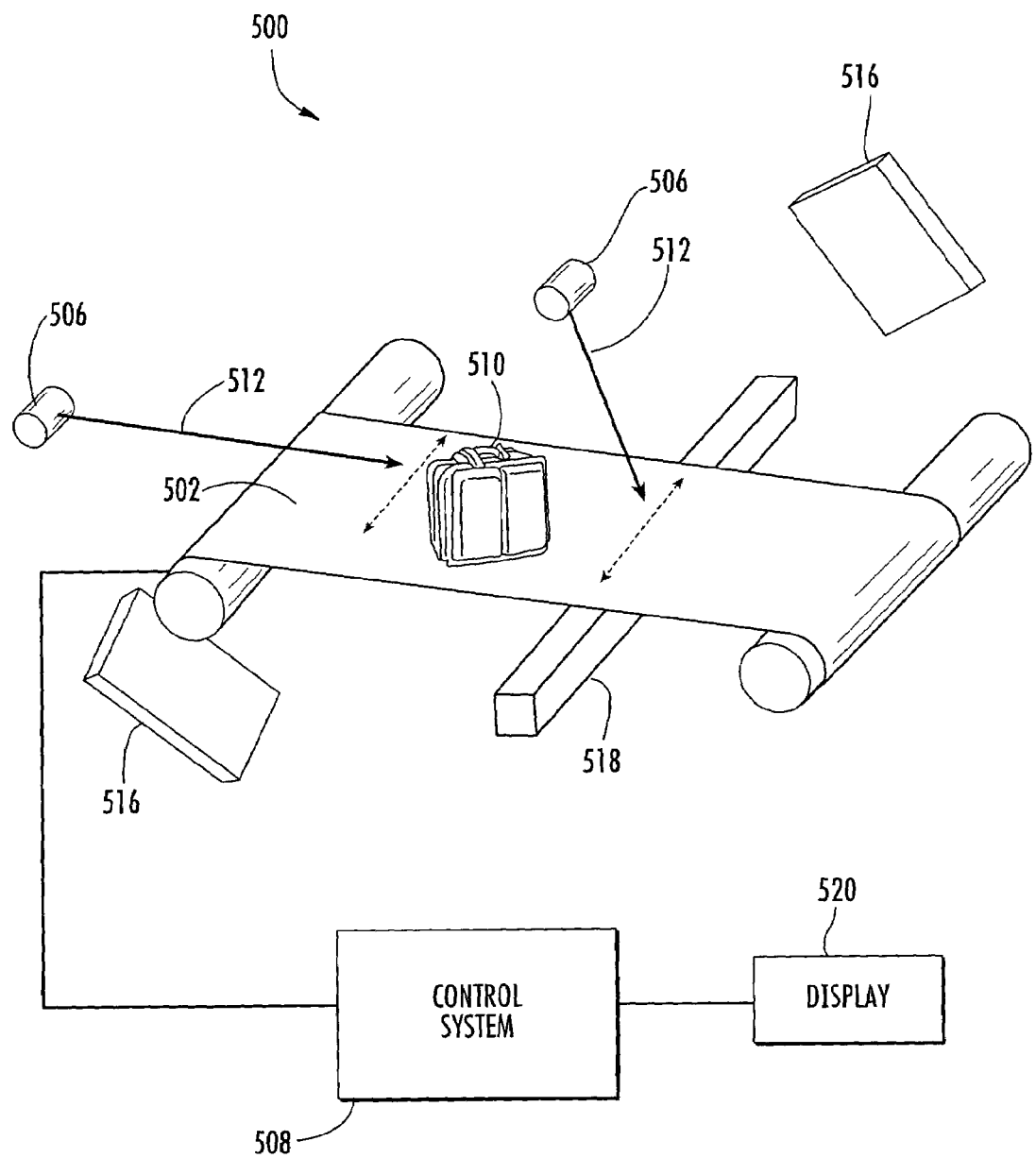
FIG. 5 is a top perspective view of an x-ray scanning system according to a further embodiment of the subject matter described herein.

In another embodiment, as shown in FIG. 5, a system 500 can comprise at least two x-ray sources configured to generate x-ray pencil beams 512 directed at an object 510 from different locations. Further, x-ray pencil beams 510 can be disposed such that they are not co-planar and are directed perpendicular to the moving direction of scanned object 510 or form another angle. The x-ray pencil beams 512 can be turned on individually one at a time. The backscatter x-ray detectors 516 can detect the scattered signal from one single source at one time. Further, the pencil x-ray beam sources 506 can be placed at different positions. A control system 508 can individually control so that pencil beams 512 can be turned on selectively in a programmable pattern. By gathering and analyzing the signals from the backscatter x-ray detectors from different x-ray pencil beams, a 3-D image of scanned object 510 can be formed to show different sides of the object on display 520.

In another embodiment, the system can scan an object with x-ray fan beams and x-ray pencil beams directed at the object from different locations. The x-ray pencil beams and x-ray fan beams can be controlled by a control system to individually turn on and off. The amplitude of the field emission current from the cold cathode inside the x-ray source can be operable to modulate to a sine, square or triangle format at different frequencies in the time domain or the emission current can be operable to modulate in the frequency domain by modulating the gate voltage. The x-ray signals from the x-ray sources therefore are modulated in the same way as the emission current of the cold cathodes. The modulated x-ray radiations can be either in the form of a pencil beam or fan beam used to scan the object. The modulated x-ray radiations can be used simultaneously or individually for imaging to decide structures, shapes, materials or positions of the same object or multi-objects at the same or different time.

In yet another embodiment, the system can scan an object and a multiplexing method can be used to obtain multiple pixels of an image simultaneously by modulating and pulsing multiple pencil beams of x-ray simultaneously. Multiple field emission based x-ray sources can be arranged in a predetermined array or pattern. Every beam of the x-ray sources can be individually controllable in terms of its frequency, intensity and duty cycles. During operation, each source can radiate the object in a distinctive way in terms of frequency, intensity or duty cycles. Multiple sources can be turned on simultaneously. The x-ray detector can record the backscatter signal from all multiple sources at the same time. By using frequency or spatial multiplexing/demultiplexing, the x-ray intensity detected can be traced back to individual sources.

According to one embodiment, a system is provided that can utilize stationary multiplex x-ray sources. A linear array of x-ray pencil beams can be generated from a multiple beam field emission x-ray (MBFEX) source, wherein each beam can be individually addressable and programmable. Each pencil beam can be responsible for one pixel in the image. This arrangement can be compact and can also increase the scanning speed. The x-ray source can be pulsed, which can reduce motion blurring and improve the image quality by reducing overlap of the pencil beam spots.

In one embodiment, a MBEFEX source with N x-ray emitting pixels can enhance the scanning speed by a factor or N/2 or better. In one aspect, all of the x-ray beams can be turned on simultaneously. Each x-ray beam can be pulsed at a different frequency. In a more specific aspect, each x-ray beam can have a square waveform and a 50% duty cycle. The frequency range of the N x-ray beams can be from between f and 3f, where f is the lowest frequency of the group. A digital detector can sample data at a rate much faster than the highest frequency of the pulsed x-ray beams. In addition, the pulse frequency of the x-ray beam needs to be comparable or higher than 1/t, where t is the total data collection time. The detector outputs temporal intensity data l(t) for all the x-ray pixel (x,y). The intensity data set can then be processed through temporal Fourier transform to obtain frequency domain spectrum $l(x, y, \omega)$. After filtering out the noise by a numerical n-band filter, n distinct principle components $d(x,y,\omega_k)$ can be obtained. The kth principle component corresponds to the x-ray generated from the x-ray source operating at $\omega_k$ frequency and is used to form the backscatter image from the kth x-ray pencil beam. Since all the beams are on at the same time, the total exposure time of the entire scan can be N/2 to N times faster than the current system.

In another aspect, the difference in the pattern of the pencil beams striking a moving object when generated by MBFEX as in the present disclosure versus those generated by a chopper and a single beam x-ray source in the existing art is substantial. For example in prior applications, assuming 1000 pixel resolution is needed across the section of an object and that each pixel requires 100 μs exposure time to get the sufficient photon count, a single line scan across the object will take 100 ms. The object would move about 30 mm laterally at the speed of 1 Km per hour during this scanning time. Therefore the effective resolution, or the effective pixel size along the moving direction is 30 mm even though the pencil beam can be much smaller such as 1 mm in diameter.

In one aspect of the subject matter disclosed herein, all 1000 beams can be turned on simultaneously. With a 50% duty cycle the scanning time will be only 200 μs scanning time, the object only moves about 0.06 mm. Therefore the resolution, or the effective pixel size can be as small as the actual size of the pencil beam. Using the multiplexing x-ray imaging method and the multi-beam field emission x-ray source, the pencil beam collimator can be larger in diameter for the same imaging resolution, and therefore it can be more efficient to use the x-ray source. The x-ray power of the x-ray tube can be reduced to extend its lifetime and save power.

FIG. 4 is a top perspective view of an x-ray scanning system generally designated 400 according to an embodiment of the subject matter described herein. System 400 can comprise multiple field-emission cold cathode-based x-ray sources. Referring to FIG. 4, system 400 can comprise a conveyor 402 and multiple independently controllable pencil beam x-ray sources 406. Also, fan beam x-ray sources can be employed independently or in conjunction with pencil beam x-ray sources 406 as illustrated in FIG. 3. Conveyor 402 can be controlled by a control system 408 to move an object 410 to be scanned in position for intercepting an x-ray pencil beam 412 (or an x-ray fan beam) emitted by x-ray sources 406. Further, system 400 can comprise backscatter x-ray detectors 416 and a transmission x-ray detector 418 operable to detect backscattered x-ray beams and transmission x-ray beams, respectively. Control system 408 can control the generation of x-ray beams by x-ray sources 406 and the detection of x-ray beams by x-ray detectors 416 and 418. More than one fan beam x-ray source and more than one pencil beam x-ray source or any combination of the two types can be utilized for applying x-ray beams to object 410.

Backscatter x-ray detectors 416 can be positioned for collecting x-rays scattered by object 410. For example, a backscatter x-ray detector placed in front of object 410, behind object 410, above object 410, or below object 410. The x-rays detected by detectors 416 can be obtained and converted into signals for use in constructing a visible image.

Transmission x-ray detector 418 can be shaped linearly for receiving transmitted x-ray beams. Alternatively, a transmission x-ray detector 418 can be formed in an "L" shape and positioned placed such that it can detect the incident x-ray after it is attenuated by scanned object 410. The x-rays detected by detector 418 can be obtained and converted into signals for use in constructing a visible image.

The x-ray sources of system 400 can comprise a plurality of pixels made of a field-emission triode and/or a diode cathode in x-ray sources for generating x-ray beams. The generated x-rays can be converted to an x-ray fan beam by using a collimator. Further, a generated x-ray fan beam can be converted to an x-ray pencil beam by applying an additional collimator or a chopper with open slots.

Control system 408 can comprise suitable hardware, software, and/or firmware components for controlling the components of system 400. System 408 can be programmed to individually control the x-ray beams emitted by x-ray sources 406, the movement of conveyor 402, the collection of signals by detectors 416 and 418, and the process, construction and analyses of the images. System 400 can comprise a display 420 for displaying images. Alternatively, system 400 can comprise a plurality of monitors for displaying different views of scanned objects.

X-ray sources 406 can be controlled by control system 408 to operate in a pulse mode for generating x-ray beam pulses of a predetermined frequency. Control system 408 can control the pixels of x-ray sources 406 to be activated at a predetermined frequency and duty cycle. The duration of the x-ray on time and the frequency of the x-ray radiation can be programmed into control system 408. In one example, the x-ray fan beam (not shown) and x-ray pencil beams 412 generated by x-ray sources 406 can be alternatively turned on at a high frequency. In this example, only one beam can be used to radiate object 410 at any one time. In this manner, the transmission x-ray signal and backscatter x-ray signal can be separated in the time domain. The signal detected by transmission x-ray detector 418 can be only from a transmission x-ray source. The signal detected by backscatter x-ray detectors 416 originates only from x-ray pencil beams 412. Therefore, both transmission x-ray images and scatter x-ray images can be available to the operator in a timely basis by switching between the two x-ray sources. By increasing the operation frequency, both kinds of images can be obtained almost simultaneously. These can be especially helpful for scanning an object having a mixture of properties.

In one embodiment, a system can comprise at least two field emission based x-ray pencil beams. The pencil x-ray beams 412 can be coplanar and placed along moving direction of object 410 to be scanned. For example, when object 410 is moving along conveyor 402, x-ray pencil beam 412 can be turned on first at time $t^1$. The scattered x-ray signals can be collected by backscatter detectors 416 during this specific time interval. As object 410 moves into the shooting range of first pencil beams 412, first pencil beam 412 can be turned on.

Therefore, additional signals from second pencil beam 412 can be recorded by the scatter x-ray detectors at time $t^2$. Imaging system 400 can operate where at most one pencil x-ray beam 412 is on at one time during the entire operation so the signals obtained by backscatter detectors 416 can be decided from a single pencil beam x-ray source 406. By knowing the time differences between $t^1$ and $t^2$, the physical distance between the two x-ray beam sources and the conveyor/object moving velocity, additional information can be acquired to reconstruct the image of scanned object 410.

FIG. 5 is a top perspective view of an x-ray scanning system generally designated 500 according to an embodiment of the subject matter described herein. System 500 can comprise multiple field-emission cold cathode-based x-ray sources. Referring to FIG. 5, system 500 can comprise a conveyor 502 and multiple independently controllable pencil beam x-ray sources 506. Also, fan beam x-ray sources can be employed independently or in conjunction with pencil beam x-ray sources 506 as illustrated in FIG. 3. Conveyor 502 can be controlled by a control system 508 to move an object 510 to be scanned in position for intercepting an x-ray pencil beam 512 (or an x-ray fan beam) emitted by x-ray sources 506. Further, system 500 can comprise backscatter x-ray detectors 516 and a transmission x-ray detector 518 operable to detect backscattered x-ray beams and transmission x-ray beams, respectively. Control system 508 can control the generation of x-ray beams by x-ray sources 506 and the detection of x-ray beams by x-ray detectors 516 and 518. More than one fan beam x-ray source and more than one pencil beam x-ray source or any combination of the two types can be utilized for applying x-ray beams to object 510.

Backscatter x-ray detectors 516 can be positioned for collecting x-rays scattered by object 510. For example, a backscatter x-ray detector placed in front of object 510, behind object 510, above object 510, or below object 510. The x-rays detected by detectors 516 can be obtained and converted into signals for use in constructing a visible image.

Transmission x-ray detector 518 can be shaped linearly for receiving transmitted x-ray beams. Alternatively, a transmission x-ray detector 518 can be formed in an "L" shape and positioned placed such that it can detect the incident x-ray after it is attenuated by scanned object 510. The x-rays detected by detector 518 can be obtained and converted into signals for use in constructing a visible image.

The x-ray sources of system 500 can comprise a plurality of pixels made of a field-emission triode and/or a diode cathode in x-ray sources for generating x-ray beams. The generated x-rays can be converted to an x-ray fan beam by using a collimator. Further, a generated x-ray fan beam can be converted to an x-ray pencil beam by applying an additional collimator or a chopper with open slots.

Control system 508 can be comprised of suitable hardware, software, and/or firmware components for controlling the components of system 500. System 508 can be programmed to individually control the x-ray beams emitted by x-ray sources 506, the movement of conveyor 502, the collection of signals by detectors 516 and 518, and the process, construction and analyses of the images. System 500 can comprise a display 520 for displaying images. Alternatively, system 500 can comprise a plurality of monitors for displaying different views of scanned objects.

X-ray sources 506 can be controlled by control system 508 to operate in a pulse mode for generating x-ray beam pulses of a predetermined frequency. Control system 508 can control the pixels of x-ray sources 506 to be activated at a predetermined frequency and duty cycle. The duration of the x-ray on time and the frequency of the x-ray radiation can be programmed into control system 508. In one example, the x-ray fan beam (not shown) and x-ray pencil beams 512 generated by x-ray sources 506 can be alternatively turned on at a high frequency. In this example, only one beam can be used to radiate object 510 at any one time. In this manner, the transmission x-ray signal and backscatter x-ray signal can be separated in the time domain. The signal detected by transmission x-ray detector 518 can be only from a transmission x-ray source. The signal detected by backscatter x-ray detectors 516 can originate only from x-ray pencil beams 512. Therefore, both transmission x-ray images and scatter x-ray images can be available to the operator in a timely basis by switching between the two x-ray sources. By increasing the operation frequency, both kinds of images can be obtained almost simultaneously. These can be especially helpful for scanning an object having a mixture of properties.

In one embodiment, a system can comprise at least two non-coplanar x-ray pencil beams 512. Two incident pencil beams 512 can be perpendicular to the moving direction of conveyor 502. The incident directions of beams 512 can be perpendicular to each other as well. Also, the incident directions of beams 512 can be parallel to each other and perpendicular to the movement of object 510. Each x-ray pencil beam 512 can be switched on and off at certain frequencies and duty cycles. The x-ray pencil beams 512 and backscatter detectors 516 can be programmed in such a way that at a specific time, the detectors can only collect the backscattered signal from one particular x-ray pencil beam 512. Because the x-ray pencil beams 512 have different incident angles to object 510, different surfaces of object 510 have a chance to scatter x-ray pencil beams 512. Therefore, the scatter images of different surfaces can be constructed. By combining the information, a high resolution three-dimensional image can be imaged.

Figure 6:
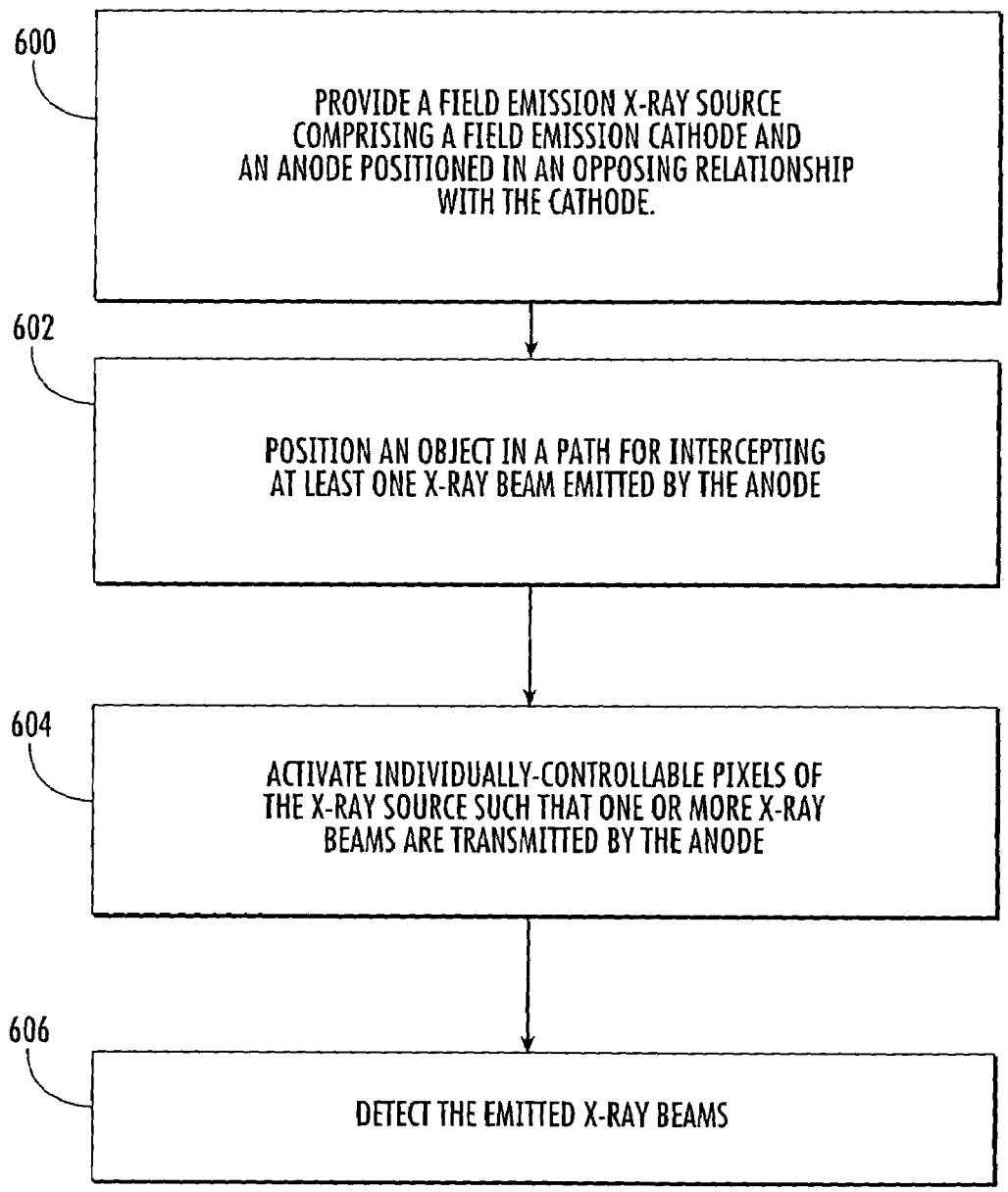
FIG. 6 is a flow chart of a method for scanning an object according to the subject matter described herein.

FIG. 6 is a flow chart of one possible method for scanning an object according to the subject matter described herein. Referring to FIG. 6, in block 600, a field emission x-ray source is provided, which can comprise a field emission cathode and an anode. The cathode includes a plurality of individually-controllable pixels configured to emit electron beams. For example, field-emission triode cathode 100 shown in FIG. 1 can include the individually-controllable pixels. The anode is positioned in an opposing relationship with the cathode and includes a plurality of focal spots positioned to receive electron beams emitted by the pixels and transmit x-ray beams toward an object to be scanned from a plurality of different locations.

In block 602, an object is positioned in a path for intercepting at least one x-ray beam emitted by the anode. For example, object 310 shown in FIG. 3 can be positioned on conveyor 302 to intercept at least one x-ray beam emitted from x-ray sources 304 and 306. In block 604, the individually-controllable pixels of x-ray sources 304 and 306 are activated such that one or more x-ray beams are transmitted by the anode. For example, referring again to FIG. 3, x-ray beams 312 and 314 can be transmitted by the anode in x-ray sources 304 and 306.

Further, in block 606, the emitted x-ray beams can be detected. For example, detectors 316 and 318 in FIG. 3 can detect emitted x-ray beams 312 and 314 from x-ray sources 304 and 306 by backscatter or transmission detection.

Figure 7:
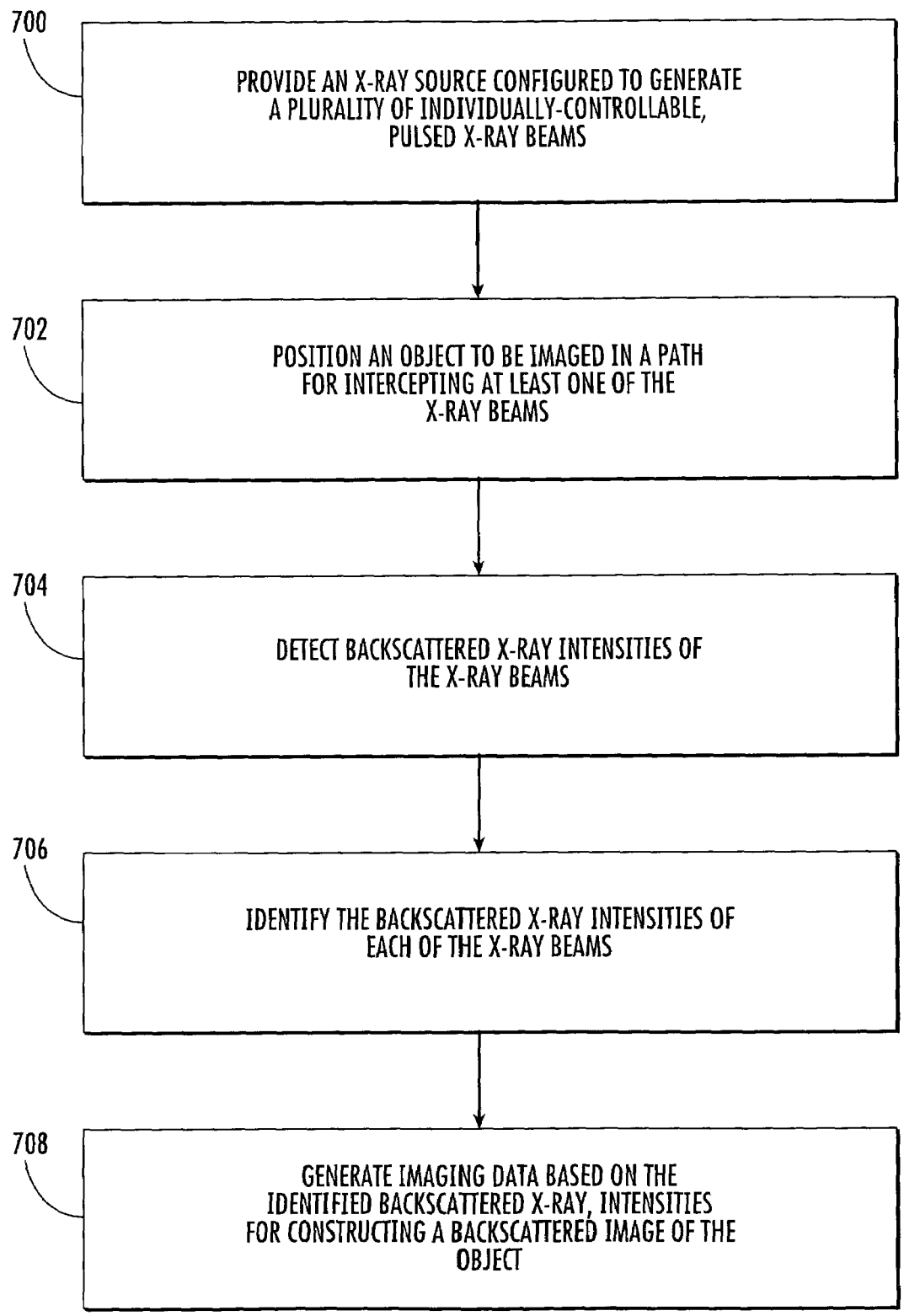
FIG. 7 is a flow chart of a method for backscatter imaging of an object according to the subject matter described herein.

FIG. 7 is a flow chart of an exemplary process for scanning an object according to an aspect of the subject matter described herein. Referring to FIG. 7, in block 700, an x-ray source is provided. The x-ray source can be configured to generate a plurality of individually-controllable, pulsed x-ray beams. In block 702, an object can be positioned to be imaged in a path for intercepting at least one of the x-ray beams. For example, as shown in FIG. 3 object 310 can be positioned on conveyor 302 such that its movement along conveyor 302 can cause object 310 to intercept at least one of the x-ray beams from x-ray source 304 and 306.

In block 704, the backscattered x-ray intensities of the x-ray beams can be detected. For example, referring again to FIG. 3, backscatter detectors 316 can detect backscattered x-ray intensities of x-ray pencil beam 314. In block 706, the backscattered x-ray intensities of each of the x-ray beams can be identified by control system 308.

Further, in block 708, imaging data can be generated based on the identified backscattered x-ray intensities for constructing a backscattered image of the object. For example, in FIG. 3 control system 308 can generate imaging data for constructing a backscattered image that can be shown on display 320. Also, x-ray detector 316 can generate data based on at least three of the detected x-ray beams 312 to construct a three-dimensional image of object 310.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. An x-ray scanning system comprising:
   (a) a field-emission x-ray source comprising:
      (i) a field-emission cathode comprising a plurality of individually-controllable pixels configured to emit multiplexed electron beams;
      (ii) an anode positioned in an opposing relationship with the cathode and comprising a plurality of focal spots positioned to receive electron beams emitted by the pixels and transmit x-ray beams toward an object to be scanned from a plurality of different locations;
   (b) an x-ray detector operable to detect x-ray intensities of each of the x-ray beams; and
   (c) a control system configured to control the x-ray source and the x-ray detector, to identify the x-ray intensities of each of the x-ray beams, and to demultiplex the identified x-ray intensities for generating imaging data.

2. The x-ray scanning system of claim 1 wherein the pixels comprise nanostructure-containing material.

3. The x-ray scanning system of claim 2 wherein the nanostructure-containing material is at least one of single-walled carbon nanotubes, multi-wall nanotubes, and mixtures of single-walled carbon nanotubes and multi-wall nanotubes.

4. The x-ray scanning system of claim 1 wherein the pixels and focal spots are arranged at least substantially linearly.

5. The x-ray scanning system of claim 1 wherein the pixels are arranged in a two-dimensional matrix.

6. The x-ray scanning system of claim 1 wherein the x-ray source is configured to generate a plurality of x-ray pencil beams.

7. The x-ray scanning system of claim 1 wherein the control system is configured to activate each of the pixels at a predetermined frequency and duty cycle.

8. The x-ray scanning system of claim 1 wherein the x-ray detector comprises a transmission x-ray detector positioned for receiving x-ray beams passing through the object to be scanned.

9. The x-ray scanning system of claim 1 wherein the x-ray detector is configured to generate data for constructing a three-dimensional image of the object.

10. The x-ray scanning system of claim 1 wherein the x-ray detector is a backscatter x-ray detector configured to detect backscattered x-ray radiation.

11. The x-ray scanning system of claim 1 further comprising a mechanical system and wherein the mechanical system is configured to move an object, and wherein the field-emission x-ray source is configured to direct the x-ray beams in a direction perpendicular to the movement of the object.

12. The x-ray scanning system of claim 1 wherein at least one of the x-ray beams is an x-ray fan beam, and wherein at least one of the x-ray beams is an x-ray pencil beam.

13. The x-ray scanning system of claim 1 wherein the x-ray detector is configured to generate data based on the detected x-ray beams for constructing a backscatter image and a transmission image of the object.

14. The x-ray scanning system of claim 1 wherein the control system is configured to modulate an electric field applied to the field-emission cathode for modulating at least two of the x-ray beams at one of different frequencies and different amplitudes, wherein the x-ray detector is configured to generate data based on the detected x-ray beams, and wherein the control system is configured to analyze the generated data based on one of the different frequencies and the different amplitudes of the x-ray beams.

15. The x-ray scanning system of claim 1 wherein the control system is configured to apply one of sine-based, cosine-based, triangle wave-based, and square wave-based modulation of a predetermined frequency and predetermined peak amplitude to the cathode.

16. A backscatter imaging system comprising:
   (a) an x-ray source comprising a plurality of individually-controllable pixels and an anode, the x-ray source configured to generate a plurality of individually-controllable, pulsed x-ray beams and configured to transmit the x-ray beams toward an object to be imaged;
   (b) a backscatter x-ray detector operable to detect backscattered x-ray intensities of the plurality of x-ray beams; and
   (c) a control system configured to identify the backscattered x-ray intensities of each of the x-ray beams and configured to generate imaging data based on the identified backscattered x-ray intensities for constructing a backscattered image of the object;
   wherein the control system is configured to activate the pixels for generating x-ray beams having at least one of a predetermined frequency, predetermined duty cycle, and predetermined intensity; and
   wherein the predetermined frequencies of the x-ray beams are orthogonal, and the control system is configured to apply a temporal Fourier transform based on orthogonal frequency division multiplexing (OFDM).

17. The system of claim 16 wherein the pixels are arranged substantially linearly.

18. The system of claim 16 wherein the pixels comprise nanostructure-containing material.

19. The system of claim 18 wherein the nanostructure-containing material is at least one of single-walled carbon nanotubes, multi-wall nanotubes, and mixtures of single-walled carbon nanotubes and multi-wall nanotubes.

20. The system of claim 16 wherein the control system is configured to:
   (a) perform temporal Fourier transformation of intensity versus time data detected by the backscatter x-ray detector;
   (b) determine the intensity contribution from each x-ray beam based on spectrum in a frequency space based on the temporal Fourier transformation; and (c) construct a plurality of backscattered images from each x-ray beam based on the determined intensity contribution.

21. The system of claim 16 wherein the x-ray source is configured for generating x-ray pencil beams, and wherein the pixels are arranged in a plurality of substantially linearly-shaped rows, wherein the control system is configured to activate rows of the pixels in accordance with a Hadamard transformation matrix.

22. A method for scanning an object, the method comprising:
  (a) providing a field-emission x-ray source comprising:
    (i) a field-emission cathode including a plurality of individually-controllable pixels configured to emit multiplexed electron beams; and
    (ii) an anode positioned in an opposing relationship with the cathode and including a plurality of focal spots positioned to receive electron beams emitted by the pixels and transmit x-ray beams toward an object to be scanned from a plurality of different locations;
  (b) positioning an object in a path for intercepting at least one x-ray beam emitted by the anode;
  (c) individually activating the pixels of the x-ray source such that one or more x-ray beams are transmitted by the anode and the electron beams are pulsed at predetermined orthogonal frequencies;
  (d) detecting x-ray intensities of each of the emitted x-ray beams;
  (e) identifying the x-ray intensities of each of the x-ray beams; and
  (f) demultiplexing the identified x-ray intensities for generating imaging data.

23. The method of claim 22 wherein the pixels comprise nanostructure-containing material.

24. The method of claim 23 wherein the nanostructure-containing material is at least one of single-walled carbon nanotubes, multi-wall nanotubes, and mixtures of single-walled carbon nanotubes and multi-wall nanotubes.

25. The method of claim 22 wherein the cathode comprises a cold cathode.

26. The method of claim 22 wherein the x-ray source is configured to generate a plurality of x-ray pencil beams.

27. The method of claim 22 wherein the x-ray beams are x-ray fan beams, and wherein the method comprises activating each of the pixels at a predetermined frequency and duty cycle.

28. The method of claim 22 comprising generating data for constructing a three-dimensional image of the object.

29. The method of claim 22 wherein detecting the emitted x-ray beams includes detecting backscattered x-ray radiation.

30. The method of claim 22 wherein detecting the emitted x-ray beams includes detecting transmission x-ray radiation.

31. The method of claim 22 comprising a mechanical system wherein the mechanical system is configured to move the object, and wherein the field-emission x-ray source is configured to direct the x-ray beams in a direction perpendicular to the movement of the object.

32. The method of claim 22 comprising a mechanical system wherein the mechanical system is configured to move the object, and wherein the field-emission x-ray source is configured to direct at least two of the x-ray beams in a direction parallel to each other and perpendicular to the movement of the object.

33. The method of claim 22 wherein at least one of the x-ray beams is an x-ray fan beam, and wherein at least one of the x-ray beams is an x-ray pencil beam.

34. The method of claim 33 wherein activating the pixels includes activating the pixels corresponding to the x-ray fan beam and the x-ray pencil beam independently.

35. The method of claim 33 comprising a mechanical system wherein the mechanical system is configured to move the object, and wherein the field-emission x-ray source is configured to direct the x-ray fan beam and the x-ray pencil beam in a direction parallel to each other and perpendicular to the movement of the object.

36. The method of claim 33 comprising generating data based on the detected x-ray beams for constructing a backscatter image and a transmission image of the object.

37. The method of claim 22 comprising modulating an electric field applied to the field-emission cathode for modulating the x-ray beams.

38. The method of claim 37 comprising modulating in different frequencies and amplitudes.

39. The method of claim 22 comprising modulating an electric field applied to the field-emission cathode for modulating at least two of the x-ray beams at one of different frequencies and different amplitudes, generating data based on the detected x-ray beams, and analyzing the generated data based on one of the different frequencies and different amplitudes of the x-ray beams.

40. The method of claim 22 wherein activating the pixels includes activating each of the pixels at a predetermined frequency and duty cycle.

41. The method of claim 22 comprising providing a plurality of discrete detectors operable to detect the x-ray beams.

42. A method for backscatter imaging an object, the method comprising:
  (a) providing an x-ray source comprising a plurality of individually-controllable pixels and an anode, the x-ray source configured to generate a plurality of individually-controllable, pulsed x-ray beams;
  (b) positioning an object to be imaged in a path for intercepting at least one of the x-ray beams;
  (c) activating the pixels for generating x-ray beams having at least one of a predetermined frequency, predetermined duty cycle, and predetermined intensity;
  (d) detecting backscattered x-ray intensities of the x-ray beams;
  (e) identifying the backscattered x-ray intensities of each of the x-ray beams;
  (f) generating imaging data based on the identified backscattered x-ray intensities for constructing a backscattered image of the object; and
  (g) applying a temporal Fourier transform based on orthogonal frequency division multiplexing (OFDM).

43. The method of claim 42 wherein the pixels comprise nanostructure-containing material.

44. The method of claim 43 wherein the nanostructure-containing material is at least one of single-walled carbon nanotubes, multi-wall nanotubes, and mixtures of single-walled carbon nanotubes and multi-wall nanotubes.

45. The method of claim 42 wherein the pixels comprise a coating layer of nanostructure-containing material on a substrate material.

46. The method of claim 42 comprising applying one of sine-based, cosine-based, triangle wave-based, and square wave-based modulation of a predetermined frequency and predetermined peak amplitude to the x-ray source.

47. The method of claim 42 comprising:
  (a) performing temporal Fourier transformation of intensity versus time data;

(b) determining the intensity contribution from each x-ray beam based on spectrum in a frequency space based on the temporal Fourier transformation; and
(c) constructing a plurality of backscattered images from each x-ray beam based on the determined intensity contribution.

48. The method of claim 42 wherein the x-ray source is configured for generating x-ray pencil beams, and wherein the pixels are arranged in a plurality of substantially linearly-shaped rows, wherein the method comprises activating rows of the pixels in accordance with a Hadamard transformation matrix, and wherein the method comprises processing the detected x-ray beams using an inversion Hadamard transformation matrix for constructing the image.

* * * * *